(12) United States Patent
Farrar et al.

(10) Patent No.: US 8,535,321 B2
(45) Date of Patent: Sep. 17, 2013

(54) SURGICAL ASSEMBLY HAVING A GUIDE BLOCK

(75) Inventors: Richard Farrar, North Rigton (GB); Callum Colquhoun, Glen Waverley (AU)

(73) Assignee: DePuy International Limited, Leeds (GB)

( * ) Notice: Subject to any disclaimer, the term of this patent is extended or adjusted under 35 U.S.C. 154(b) by 1297 days.

(21) Appl. No.: 10/524,800

(22) PCT Filed: Aug. 11, 2003

(86) PCT No.: PCT/GB03/03496
§ 371 (c)(1),
(2), (4) Date: Jan. 17, 2006

(87) PCT Pub. No.: WO2004/017843
PCT Pub. Date: Mar. 4, 2004

(65) Prior Publication Data
US 2006/0155291 A1 Jul. 13, 2006

(30) Foreign Application Priority Data
Aug. 20, 2002 (GB) .................................. 0219342.3

(51) Int. Cl.
*A61F 5/00* (2006.01)
(52) U.S. Cl.
USPC ........................................................ 606/87
(58) Field of Classification Search
USPC .......................................... 606/86–89, 96, 98
See application file for complete search history.

(56) References Cited

U.S. PATENT DOCUMENTS

| 4,457,307 | A | | 7/1984 | Stillwell | |
|---|---|---|---|---|---|
| 4,703,751 | A | * | 11/1987 | Pohl | 606/62 |
| 4,952,213 | A | | 8/1990 | Bowman et al. | |
| 5,108,396 | A | * | 4/1992 | Lackey et al. | 606/62 |
| 5,342,368 | A | * | 8/1994 | Petersen | 606/88 |
| 5,681,316 | A | * | 10/1997 | DeOrio et al. | 606/88 |
| 5,688,283 | A | | 11/1997 | Knapp | |
| 5,688,284 | A | | 11/1997 | Chervitz et al. | |
| 5,749,876 | A | | 5/1998 | Duvillier et al. | |
| 5,833,693 | A | | 11/1998 | Abrahami | |
| 5,911,723 | A | | 6/1999 | Ashby et al. | |
| 6,174,314 | B1 | * | 1/2001 | Waddell | 606/88 |
| 6,554,837 | B1 | * | 4/2003 | Hauri et al. | 606/87 |
| 7,377,924 | B2 | * | 5/2008 | Raistrick et al. | 606/87 |

(Continued)

FOREIGN PATENT DOCUMENTS

DE 297 04 393 U1 7/1997
EP 0 774 238 A1 5/1997

(Continued)

*Primary Examiner* — Nicholas Woodall
(74) *Attorney, Agent, or Firm* — Maginot, Moore & Beck

(57) ABSTRACT

A guide block for use in surgery to locate a surgical tool accurately relative to an anatomical feature comprises a fixation part which can be fastened directly to the patient's tissue, and a guide part having at least one structural feature to engage a surgical tool to ensure that the tool is located appropriately relative to the patient's tissue. The guide part is mounted on the fixation part. The guide block includes at least two drives for adjusting the position of the guide part relative to the fixation part, so that the position of the guide part relative to the fixation part can be adjusted in at least two degrees of freedom. The fixation part of the guide block includes a housing which is hollow, and the drives are located inside the housing.

13 Claims, 2 Drawing Sheets

(56) References Cited

U.S. PATENT DOCUMENTS

| | | |
|---|---|---|
| 2001/0018589 A1* | 8/2001 | Muller .......................... 606/88 |
| 2002/0133163 A1* | 9/2002 | Axelson et al. ............... 606/88 |
| 2002/0198531 A1 | 12/2002 | Millard et al. |
| 2003/0069585 A1* | 4/2003 | Axelson et al. ............... 606/88 |
| 2005/0021039 A1* | 1/2005 | Cusick et al. ................. 606/88 |

FOREIGN PATENT DOCUMENTS

| | | |
|---|---|---|
| EP | 0 809 969 A2 | 12/1997 |
| EP | 0 809 969 B1 | 12/1997 |
| EP | 1 269 924 A1 | 1/2003 |
| FR | 2 776 176 A1 | 9/1999 |
| WO | WO 0000093 A1 * | 1/2000 |

* cited by examiner

SURGICAL ASSEMBLY HAVING A GUIDE BLOCK

This invention relates to a guide block which can be used in surgery, especially orthopaedic surgery, to locate a surgical tool accurately.

Surgical instruments are commonly used to locate a tool accurately during the course of a surgical procedure. In orthopaedic procedures which involve implanting a joint prosthesis, this can be important to ensure correct alignment of the prosthesis. For example, it is generally required to resect a patient's natural bone in a procedure to implant a prosthesis, and reliable performance of the prosthesis requires that the bone is resected accurately.

Accurate location of a tool can be achieved by means of a guide block. This can include one or more structural features which can be engaged by the tool. The guide block is fastened to the patient's bone, so that the tool can be positioned against the structural features which can provide a point of reference for locating the tool. For example, when the tool is a saw, the structural feature can be a surface, or a pair of surfaces which define a slot, against which the saw blade is moved. When the tool is a drill, the structural feature can comprise an opening in which a drill bit can be inserted.

In order for the guide block to be able to provide accurate location of a tool, it is vitally important for the structural feature(s) of the guide block to be located accurately relative to the patient's anatomical features. The desired location of the structural feature(s) can be determined during pre-operative planning with reference to images of the patient's anatomy. It can also be determined intra-operatively based on exposed bones. Fixing of a guide block to a patient's bone is commonly achieved using bone screws or pins or both, which can be inserted into pre-drilled holes. However, especially in the absence of a stabilising device such as an ankle clamp, it can be difficult to determine the appropriate positions for the bone screws and inaccurate positioning of the bone screws leads to inaccurate positioning of the guide block and therefore also of the relevant structural features.

The present invention provides a guide block which comprises a fixation part and a guide part, which can be moved relative to the fixation part by means of a drive unit.

Accordingly, in one aspect, the invention provides a guide block for use in surgery to locate a surgical tool accurately relative to an anatomical feature, which comprises a fixation part which can be fastened directly to the patient's tissue, and a guide part having at least one structural feature to engage a surgical tool to ensure that the tool is located appropriately relative to the patient's tissue, the guide part being mounted on the fixation part, the guide block including at least one indexed drive by which the position of the fixation part relative to the guide part can be adjusted.

The guide block of the invention has the advantage that it provides for locating the structural feature engaged by the surgical tool separately from fixing the guide block to the patient's tissue. The fixation part of the guide block can be fixed to the patient's tissue in a first step, and any inaccuracy in its location can be corrected by subsequent movement of the guide part relative to the fixation part using the drive. This has the advantage of greatly simplifying the fixation of a guide block to a patient's bone or other tissue. It can also provide for significantly greater accuracy in the location of the structural feature of the guide block relative to landmarks on the patient's anatomy.

In the guide block of the invention, the structural feature can comprise a guide surface which can be engaged by a cutting tool such as a blade to define the appropriate alignment for a cut. When the guide surface is planar, it will define a cutting plane. However, it can be curved or otherwise non-planar, so that the patient's tissue is cut along a curved line. It might also have two parts which define separate cut lines, which might but need not intersect. The structural feature can comprise a pair of closely spaced guide surfaces which define between them a slot in which a blade can be inserted.

The structural feature can comprise an opening in which a drill bit can be inserted. The guide part of the block can provide more than one opening for a drill bit, for example two or three openings. The guide block of the invention can be used in this way to locate accurately a position for an implant, or for another surgical tool which is to be fastened to a patient's bone or other tissue, for example by means of screws.

The fixation part of the guide block can be fastened to the patient's bone or other tissue by means of at least one fastener, generally two or three fasteners. Suitable fasteners might include, for example, pins or screws. It can therefore be preferred for the fixation part to have at least one opening, preferably a plurality of openings, extending through it in which one or more fasteners can be located for fixing the part to the patient's tissue.

Preferably, the fixation part of the guide block includes a housing which is hollow, and the drives are located inside the housing. Preferably, the guide block includes connector shafts which extend from the fixation part to the guide part, which are moved relative to the fixation part by respective ones of the drives to cause the location of the guide part to be adjusted. Preferably, the fixation part includes means for adjusting the drives which are accessible from outside the housing. For example, the drives might be adjusted by means of externally mounted knobs, or the housing might include connectors for pneumatic control or to engage an external mechanical drive. The housing can include openings which extend through it which can receive fasteners (for example screws or pins) by which the housing can be fastened to a bone. Alternatively, the housing can include a clamp by which it can be fastened to a bone.

Preferably, the drive includes at least one threaded shaft on one of the fixation part and the guide part, and a threaded bore in the other of the fixation part and the guide part. The threaded shaft can be received in the threaded bore so that the position of the guide part relative to the fixation part can be adjusted by rotating the shaft relative to the bore. Generally, it will be preferred for the shaft to be fastened to one of the fixation part and the guide part in a way which allows it to be rotated relative to that part, and for the threaded bore to be fixed. The shaft can be fixed by means of cooperating rib and groove. For example, the shaft can have a groove extending around its circumference, in which a rib on the fixation part or the guide part protrudes. The groove can be provided by two parts of the shaft which, when assembled together, provide opposite surfaces which can engage the rib between them. One part of the shaft can be a screw which is received in a bore in the other part of the shaft.

The drive can operate pneumatically, for example using a fluid delivery line and a reservoir, in which the amount of fluid or the pressure of the fluid can be adjusted to change the relative positions of the fixation and guide parts.

The drive can include a knob which can be engaged manually to cause relative rotation between the shaft and the bore.

The guide block can include a flexible drive shaft which can be connected to the guide part, through which rotational motion can be imparted to the guide part from a remote location to cause relative rotation between the shaft and the bore. For example, rotational motion can be provided by an external motor. Rotational motion might also be provided manually and transmitted to the guide block by means of the drive shaft.

It will generally be preferred for the guide block to include at least two drives for adjusting the position of the guide part relative to the fixation part, so that the position of the guide part relative to the fixation part can be adjusted in at least two degrees of freedom. It will often be particularly preferred for the guide block to include at least three drives so that the position of the guide part relative to the fixation part can be adjusted in three or more degrees of freedom, for example four or five degrees of freedom.

The guide block can include an electric motor for causing relative rotation between the shaft and the bore. The motor can be provided within the guide block, for example in the fixation part. Alternatively, the motor can be outside the guide block. Drive from the motor to the guide block can be provided by means of a suitable drive shaft connector.

Preferably, the guide block includes at least one position indicator which is fixed relative to the guide part, and at least one position monitor for tracking the location of the position indicator, so that the position of the guide part relative to a reference point can be determined. The guide block will preferably include three (or more) position indicators so that the location and orientation of the guide part can be determined accurately. As clearly shown in FIG. 2, the position indicators are supported by the guide part. Position indicators which can be used in surgical procedures are known. Suitable position indicators include passive indicators which are reflective and emitting indicators such as those which comprise one or more light emitting diodes. A guide block with one or more position indicators can be used in a system which includes a position detector which can detect signals from the position indicator, and determine the location and/or orientation of the guide part relative to a reference coordinate system. Preferably, the system will include position detectors which provide signals to allow the location and/or orientation of the patient to be determined as well.

The guide block can be provided as part of a drive system for use in surgery, which also includes a signal generator which is connected to the drive, for generating position signals which are transmitted to the drive to cause the guide part to move relative to the fixation part.

The guide block of the invention finds particular in orthopaedic surgery where accurate positioning of instruments used in surgery, and of prosthesis components, is vitally important. For example, the guide block of the invention can be used to locate a saw relative to anatomical features, especially on a bone, for a resection step. For example, it can be used to locate the plane for the resection of the tibia in the implantation of a knee joint prosthesis. In this procedure, a guide block will have a surface against which a saw blade can be positioned, especially a pair of surfaces which define a slot. The guide block is fastened to the tibia in approximately the correct location relative to previously identified anatomical landmarks, for example by three bone screws which pass through fixation holes in the fixation part of the block. The guide block will include three drives by which the location of the guide part can be adjusted relative to the fixation part. A first drive can adjust the anterior-posterior tilt of the guide part. The second drive can adjust the medial-lateral tilt of the guide part. The third drive can adjust the spacing between the guide and fixation parts along a desired axis, for example essentially along the patient's anatomical axis.

The guide block of the invention will preferably be made from a metallic material, such as used conventionally for surgical instruments. Examples of suitable materials include certain stainless steels.

Embodiments of the present invention will now be described by way of example with reference to the accompanying drawings in which.

Figure 1:
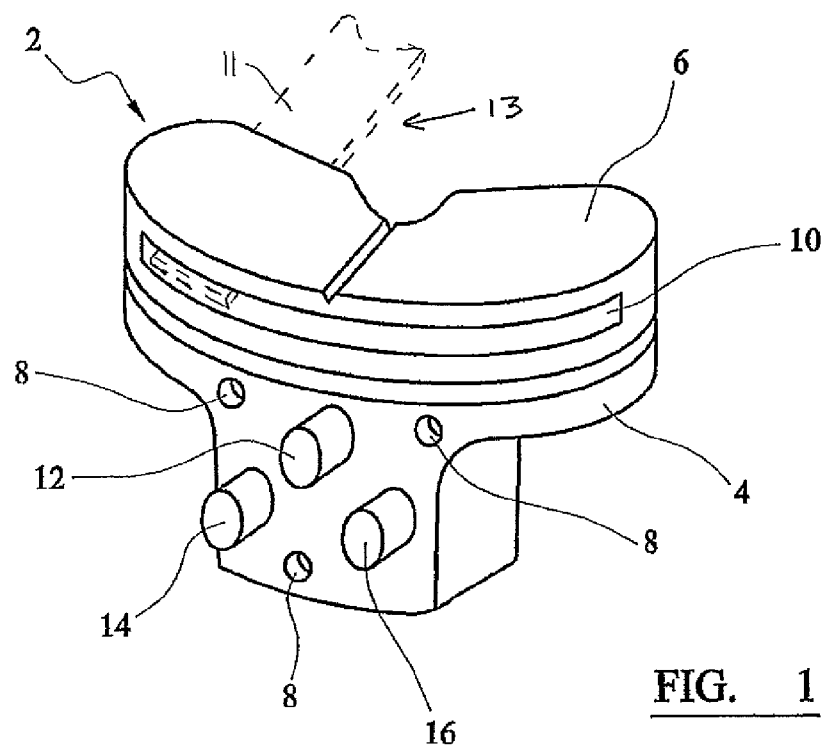
FIG. 1 is an isometric view showing a guide block according to the present invention, which can be used to locate the tibial resection plane in a surgical procedure to implant a knee joint prosthesis.

Referring to the drawings, FIG. 1 shows a guide block 2 which comprises a fixation part 4 and a guide part 6. The fixation part 4 has three holes 8 extending through it by which it can be fixed to a patient's tibia by means of bone screws. The location for fixing the fixation part of the guide block to the tibia can be determined with reference to anatomical landmarks which are identified in pre-operative planning stages of the surgical procedure.

The guide part 6 of the fixation block has a slot 10 in it. The slot extends through the guide part so that a blade 11 of a surgical tool 13 (schematically shown in phantom) inserted into the slot can extend through it and be used to cut a bone to which the guide block is fixed. The slot will be dimensioned so that the blade is a sliding fit, as in existing cutting blocks.

The location and orientation of the resection plane is determined by the position of the slot 10 relative to the patient's bone. This can be adjusted by movement of the guide part 6 of the cutting block relative to the fixation part 4.

The fixation part has three control knobs on it. Each of them forms part of a drive which can be used to adjust the location and orientation of the guide part relative to the fixation part. A first knob 12 is used to adjust the anterior-posterior tilt of the guide part. A second knob 14 is used to adjust the medial-lateral tilt of the guide part. A third knob 16 is used to adjust the spacing between the guide and fixation parts, essentially along the patient's anatomical axis.

Figure 3:
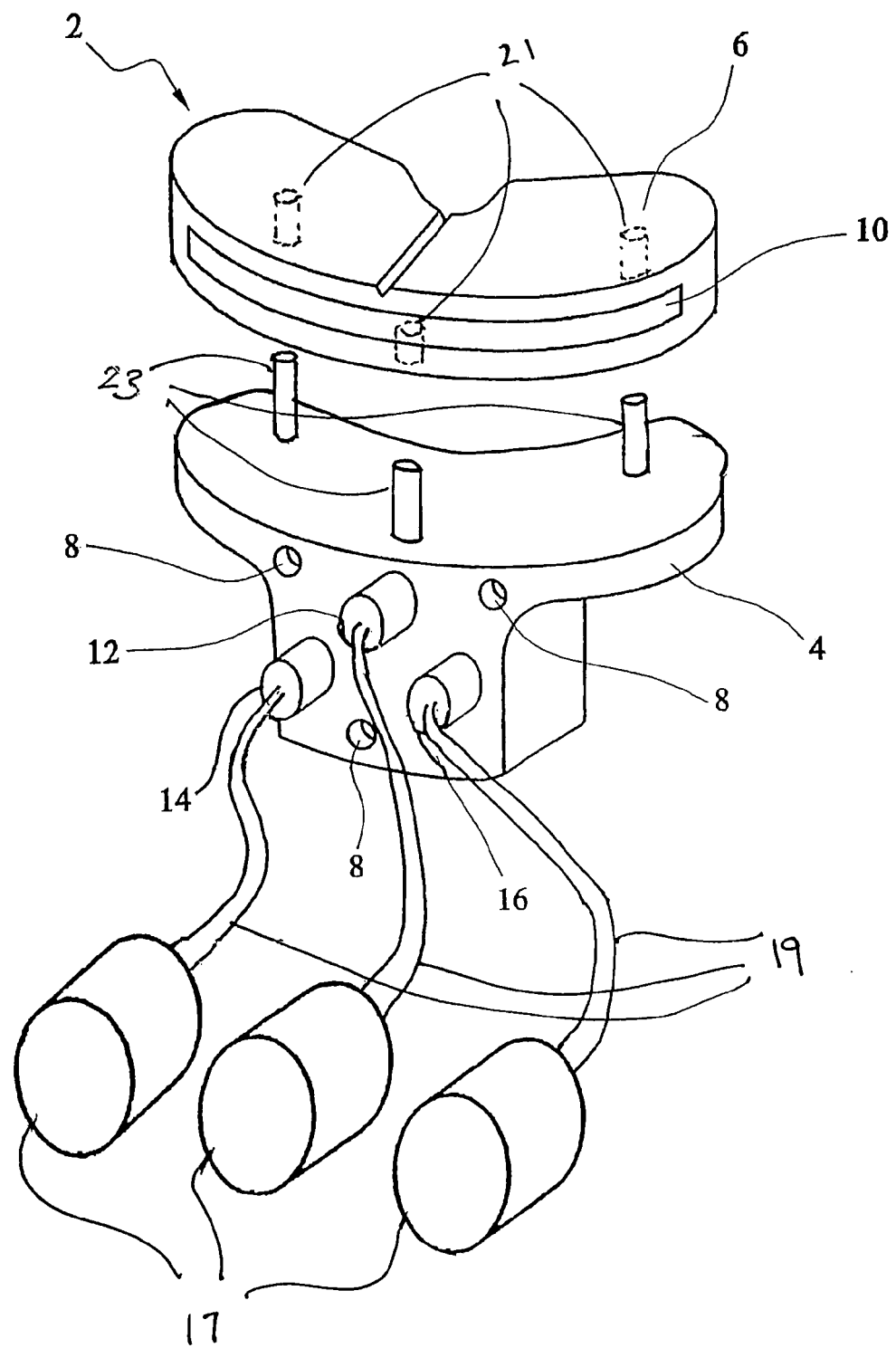
FIG. 3 is an isometric view of yet another embodiment of guide block according to the present invention.

Remote operation of the drives can be achieved using flexible drive shafts 19 which are connected to move the guide part of the guide block as shown in FIG. 3. For example, a drive shaft 19 having a hexagonal male part can be received in a hexagonal socket on the fixation part of the guide block. The drive shaft 19 can be operated manually, remotely of the guide block. Alternatively, the drive shaft 19 can be driven remotely by a motor 17 as shown in FIG. 3.

Further referring to FIG. 3 there is shown a guide block which has a drive including a plurality of threaded shafts 23 on the fixation part and a plurality of threaded bores 21 in the guide part in which the threaded shafts can be received. FIG. 3 also shows the flexible drive shafts 19 described above.

Figure 2:
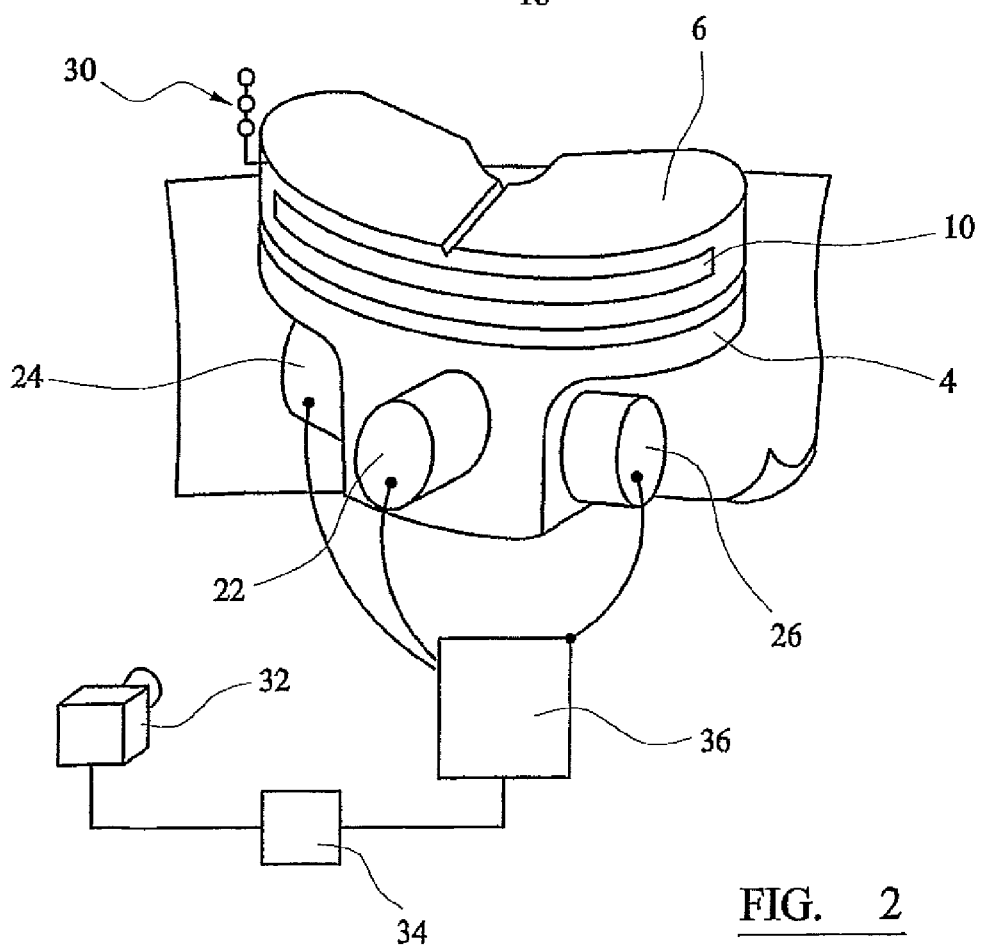
FIG. 2 is an isometric view of another embodiment of guide block according to the present invention.

FIG. 2 shows a guide block which is similar to that shown in FIG. 1. However, instead of having knobs 12, 14, 16 to control the movement of the fixation part 4 relative to the guide part 6, the block includes three motors 22, 24, 26. Signals are supplied to the motors from a signal generator to cause them to move the guide part of the guide block.

The guide part additionally includes three position indicators 30. Each of the position indicators can comprise an array of light emitting diodes as known for use in navigation systems used in surgical procedures. Other position indicators are known.

The guide block shown in FIG. 2 is used as part of a computer assisted surgical navigation system including position indicators (not shown) which can be fixed to the patient's bone to allow information to be generated about the location and orientation of the bone. The system further includes a position detector 32 which can detect signals from the position indicators. Data that is derived from the position indicators using the position detector can be used to generate information as to the positions of the bone and the guide part, using a computer 34. The computer also includes a signal generator 36 by which drive signals for the motors 22, 24, 26 can be generated. If it is determined that the guide part is not located or oriented appropriately relative to the bone, its location and/or orientation can be adjusted by providing signals to the motors 22, 24, 26 by means of the signal generator.

The invention claimed is:

1. A surgical assembly comprising:
   a guide block which comprises:
   a. a fixation part configured to be fastened directly to a patient's tissue, and
   b. a guide part having at least one tool engagement guide surface, the guide part being mounted in relation to the fixation part,
   c. at least two drives configured to adjust the position of the guide part relative to the fixation part, so that the position of the guide part relative to the fixation part can be adjusted in at least two degrees of freedom, and
   d. at least one position indicator which is supported by and fixed relative to the guide part,
   at least one position monitor configured to track the location of the position indicator, so that the position of the guide part relative to a reference point can be determined,
   a signal generator which is connected to the drives and configured to generate position signals which are transmitted to the drives to cause the guide part to be moved relative to the fixation part to a desired position relative to the reference point; and
   a surgical tool having a bone contacting cutting structure positioned in engagement with the tool engagement guide surface of the guide part during use of the surgical tool.

2. A surgical assembly as claimed in claim 1, in which the guide block includes at least three drives configured to adjust the position of the guide part relative to the fixation part, so that the position of the guide part relative to the fixation part can be adjusted in at least three degrees of freedom.

3. A surgical assembly as claimed in claim 1, in which the fixation part of the guide block includes a housing which is hollow, and in which the drives are located inside the housing.

4. A surgical assembly as claimed in claim 1, in which the guide block includes connector shafts which extend from the fixation part to the guide part, which are moved relative to the fixation part by respective ones of the drives to cause the location of the guide part to be adjusted.

5. A surgical assembly as claimed in claim 1, in which the fixation part includes means for adjusting the drives which are accessible from outside the housing.

6. A surgical assembly as claimed in claim 1, in which the bone contacting cutting structure of the surgical tool is a saw blade.

7. A surgical assembly as claimed in claim 1, in which the bone contacting cutting structure of the surgical tool is a drill bit.

8. A surgical assembly as claimed in claim 1, in which the fixation part has at least one opening extending through it in which a fastener can be located for fixing the fixation part to the patient's tissue.

9. A surgical assembly as claimed in claim 8, in which the fixation part has a plurality of openings extending through it in which fasteners can be located for fixing the fixation part to the patient's tissue.

10. A surgical assembly as claimed in claim 1, in which at least one of the drives includes at least one threaded shaft on one of the fixation part and the guide part, and a threaded bore in the other of the fixation part and the guide part in which the threaded shaft can be received, in which the position of the guide part relative to the fixation part can be adjusted by rotating the at least one threaded shaft relative to the threaded bore.

11. A surgical assembly as claimed in claim 10, in which the at least one of the drives includes a knob which can be engaged manually to cause relative rotation between the at least one threaded shaft and the threaded bore.

12. A surgical assembly as claimed in claim 10, in which the guide block further includes an electric motor configured to cause relative rotation between the at least one threaded shaft and the threaded bore.

13. A surgical assembly as claimed in claim 10, in which the guide block further includes a flexible drive shaft connected to the guide part, through which rotational motion can be imparted to the guide part from a remote location to cause relative rotation between the at least one threaded shaft and the threaded bore.

* * * * *